United States Patent [19]

Bernstein et al.

[11] Patent Number: 6,090,824

[45] Date of Patent: Jul. 18, 2000

[54] THERAPEUTIC NEUROKININ RECEPTOR ANTAGONIST COMPOUNDS

[75] Inventors: Peter R. Bernstein, Wallingford, Pa.; Bruce T. Dembofsky, Newark, Del.

[73] Assignee: Zeneca Limited, United Kingdom

[21] Appl. No.: 08/749,130

[22] Filed: Nov. 14, 1996

[30] Foreign Application Priority Data

Nov. 17, 1995 [GB] United Kingdom .................... 9523526

[51] Int. Cl.⁷ .......................... A01N 43/40; C07D 211/08; C07D 211/78; C07D 401/00

[52] U.S. Cl. .......................... 514/317; 514/256; 514/318; 514/322; 514/324; 514/326; 514/329; 514/330; 514/331; 544/242; 544/333; 544/335; 546/187; 546/188; 546/189; 546/190; 546/191; 546/192; 546/200; 546/208; 546/209; 546/216; 546/217; 546/221; 546/229; 546/232; 546/233; 546/236; 546/237; 546/238; 546/240; 546/256; 546/318; 546/322; 546/324; 546/326; 546/327; 546/331

[58] Field of Search ...................................... 546/225, 226, 546/192, 187, 188, 189, 190, 191, 200, 208, 209, 216, 217, 221, 229, 232, 233, 236, 237, 238, 290; 514/826, 317, 330, 256, 318, 322, 324, 326, 327, 331; 544/242, 333, 335

[56] References Cited

U.S. PATENT DOCUMENTS

| | | | |
|---|---|---|---|
| 4,782,061 | 11/1988 | Kruse et al. ............................. | 514/254 |
| 5,236,921 | 8/1993 | Emonds-Alt et al. ................... | 514/252 |
| 5,340,822 | 8/1994 | Emonds-Alt et al. ................... | 514/316 |
| 5,411,971 | 5/1995 | Edmonds-Alt et al. ................ | 514/318 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0 099 148 | 1/1984 | European Pat. Off. . |
| 0428434 | 5/1991 | European Pat. Off. . |
| 0474561 | 3/1992 | European Pat. Off. . |
| 0512901 | 11/1992 | European Pat. Off. . |
| 0512902 | 11/1992 | European Pat. Off. . |
| 0515240 | 11/1992 | European Pat. Off. . |
| 0559538 | 9/1993 | European Pat. Off. . |
| 0625509 | 11/1994 | European Pat. Off. . |
| 0630887 | 12/1994 | European Pat. Off. . |
| 0680962 | 11/1995 | European Pat. Off. . |
| 0709375 | 5/1996 | European Pat. Off. . |
| 0709376 | 5/1996 | European Pat. Off. . |
| 0739891 | 10/1996 | European Pat. Off. . |
| 1 510 206 | 1/1968 | France . |
| 2 496 653 | 6/1982 | France . |
| 1545670 | 8/1969 | Germany . |
| 59-193880 | 11/1984 | Japan . |
| 59-212483 | 12/1984 | Japan . |
| 923177 | 1/1993 | South Africa . |
| 923178 | 1/1993 | South Africa . |
| WO 94/10146 | 5/1994 | WIPO . |
| WO 94/29309 | 12/1994 | WIPO . |
| WO 95/05377 | 2/1995 | WIPO . |
| WO 95/12577 | 5/1995 | WIPO . |
| WO 95/15961 | 6/1995 | WIPO . |
| WO 95/16682 | 6/1995 | WIPO . |
| WO 95/21821 | 8/1995 | WIPO . |
| WO 96/24582 | 8/1996 | WIPO . |

OTHER PUBLICATIONS

A. Graham et al., "Isolation and Characterisation of the Human Lung NK–2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR 48968, a Non–Peptide Antagonist of the Neurokinin A (NK2) Receptor", *Biorganic & Medicinal Chemistry Letters*, (1993), vol. 3, No. 5, 925–930.

D. Aharony et al., "Pharmacologic Characterization of the Novel Ligand [4,5–3H–LEU9]Neurokinin–A Binding to NK–2 Receptors on Hamster Urinary Bladder Membranes", *Neuropeptides*, (1992), 23, 121–130.

M. Needham et al., "LCR/MEL: A Versatile System for High–Level Expression of Heterologous Proteins in Erythroid Cells", *Nucleic Acids Research*, (1992), vol. 20, No. 5, 997–1003.

M. Ichinose et al., "Protection against bradykinin–induced bronchoconstriction in asthmatic patients by neurokinin receptor antagonist", *The Lancet*, (1992), vol. 340, 1248–1251.

Srulevitch, David B. et al: "Design, Synthesis and Sar of Analgesics", Progress in Clinical and Biological Research, *QSAR: Quantitative Structure–Activity Relationships in Drug Design*, (1989), 291, pp. 377–381.

Nikolova, M. et al: "Synthesis and Pharmacological Screening of a Group of Piperazine Derivatives. Analgesic Activity", *Il Farmaco* (1993), 48(4), vol. XLVII, pp. 459–472.

Zhu, Ying–Qi: CA: 95 (17): 150311C; Studies on Potent Analgesics. I. Synthesis and Analgesic Activity of Fentanyl Derivatives. Yao Hsueh Hsueh Pao 1981, 16(3), 199–210 (CH.).

Igarashi et al, Chemical Abstrats vol. 70 No. 52912. "Synthesis and Pharmacology of Basic, Sec–, and Tert–Alcohol and Derivatives", (1973).

Barbatown et al, Chemical Abstract vol. 76 No. 126542 "Syn. of Alkyomivally Estes of Benzylakamin Alkymaunk Acct Dr." 1971.

Jonczyk et al, Chemical Abstract vol. 79 NO. 4959, "Vention of Organic Onions"1973.

Kametami et al, Chemical Abstract vol. 76 No. 94617, "Antispasmodic Agents"1971.

*Primary Examiner*—Alan L. Rotman
*Assistant Examiner*—Raymond Covington
*Attorney, Agent, or Firm*—Richard V. Person

[57] ABSTRACT

Compounds of formula I

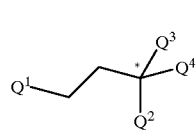

wherein $Q^1$, $Q^2$, $Q^3$, and $Q^4$ have any of the meanings given in the specification, their N-oxides, and their pharmaceutically acceptable salts are nonpeptide antagonists Substance P and NKA, useful for the treatment of asthma, etc. Also disclosed are pharmaceutical compositions, processes for preparing the compounds of formula I and intermediates.

16 Claims, No Drawings

THERAPEUTIC NEUROKININ RECEPTOR ANTAGONIST COMPOUNDS

This invention concerns novel piperidine derivatives which antagonize the pharmacological actions of the endogenous neuropeptide tachykinins known as neurokinins, particularly at the neurokinin 1 (NK1) and the neurokinin 2 (NK2) receptors. The novel piperidine derivatives are useful whenever such antagonism is desired. Thus, such compounds may be of value in the treatment of those diseases in which the NK1 and/or NK2 receptor is implicated, for example, in the treatment of asthma and related conditions. The invention also provides pharmaceutical compositions containing the novel piperidine derivatives for use in such treatment, methods for their use, and processes and intermediates for the manufacture of the novel piperidine derivatives.

The mammalian neurokinins comprise a class of peptide neurotransmitters which are found in the peripheral and central nervous systems. The three principal neurokinins are SP (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, the receptors are classified as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Thus, the tachykinins are implicated in the pathophysiology and airway hyperresponsiveness observed in asthmatics; and blockade of the action of released tachykinins may be useful in the treatment of asthma and related conditions. A cyclopeptide antagonist (FK-224) selective for both NK1 and NK2 receptors has demonstrated clinical efficacy in human patients suffering from asthma and chronic bronchitis. M. Ichinose, et al., *Lancet*, 1992, 340, 1248. Nonpeptidic tachykinin antagonists have been reported, for example in European Patent Application, Publication Number (EPA) 428434, EPA 474561, EPA 512901, EPA 512902, EPA 515240 and EPA 559538, as well as in WO 94/10146, EPA 0625509, EPA 0630887, EPA 680962, WO 95/05377, WO 95/12577, WO 95/15961, and WO 95/16682. We have discovered a series of non-peptidic antagonists of the NK1 and NK2 receptors, and this is the basis for our invention.

According to the invention, there is provided a Compound of the invention which is a compound of formula I (formula set out hereinbelow following the Examples, together with other formulae denoted by Roman numerals) wherein $Q^1$ is a radical selected from the group of radicals of formulae Ia, Ib, Ic, Id, Ie, If, Ig, Ih, Ij, Ik, and Im wherein for a radical of formula Ia, $Z^a$ is nitrogen or a group $CR^{ad}$ in which $R^{ad}$ is hydrogen or $R^{ad}$ together with $R^{ac}$ and the existing carbon to carbon bond forms a double bond; $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical —$(CH_2)_j$— in which j is an integer from 1 to 5; or $R^{ab}$ and $R^{ac}$ together form a diradical —$(CH_2)_k$— in which k is an integer from 2 to 6, or $R^{ab}$ and $R^{ac}$ together are oxo or dialkylaminoalkyloxyimino of formula =N—O—$(CH_2)_q$—$NR^{ae}R^{af}$ in which q is the integer 2 or 3 and $R^{ae}$ and $R^{af}$ are independently hydrogen or (1–4C) alkyl, or the radical $NR^{ae}R^{af}$ is pyrrolidino, piperidino or morpholino;

for a radical of formula Ib, $Z^b$ is a substituted imino group $R^{ba}N$ or $R^{ba}CH_2N$ in which $R^{ba}$ is (3–7C)cycloakyl, Ar or Het; or $Z^b$ is a disubstituted methylene group $R^{bb}$ $(CH_2)_p$—C—$R^{bc}$ in which $R^{bb}$ is Ar or Het; p is the integer 0 or 1; and $R^{bc}$ is hydrogen, hydroxy, 1–4C) alkoxy, 1–4C)alkanoyloxy, $COOR^{bd}$ (wherein $R^{bd}$ is hydrogen or (1–3C)alkyl), cyano, $NR^{be}R^{bf}$ or $SR^{bg}$ in which $R^{bc}$ and $R^{bf}$ are independently hydrogen, (1–4C) alkyl, (1–4C)hydroxyalkyl or 1–4C)alkanoyl, or the radical $NR^{be}R^{bf}$ is pyrrolidino, piperidino or morpholino; and $R^{bg}$ is hydrogen or 1–4C)alkyl; or $R^{bc}$ forms a double bond with the carbon atom to which it is bonded and with the adjacent carbon atom in the piperidine ring;

for a radical of formula Ic, $R^{ca}$ is Ar or Het; and $Z^c$ is oxo, thio, sulfinyl, sulfonyl or imino of formula —$NR^{cb}$— in which $R^{cb}$ is (1–3C)alkyl or $R^{cc}R^{cd}N$—$(CH_2)_q$—in which q is the integer 2 or 3 and in which $R^{cc}$ and $R^{cd}$ are independently hydrogen or (1–3C)alkyl or the radical $R^{cc}R^{cd}N$ is pyrrolidino, piperidino or morpholino;

for a radical of formula Id, $R^{da}$ is 1, 2 or 3;

for a radical of formula Ie, $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C) cycloalkyl, or the radical $NR^{ed}R^{ee}$ is pyrrolidino, piperidino, morpholino, thiomorpholino (or its S-oxide) or piperazinyl (which piperazinyl group may bear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis, cis-butadienylene, pentamethylene and cis-pentenylene which divalent group $L^f$ itself may bear one or two methyl substituents;

for a radical of formula Ig, $Z^g$ is (1–8C)alkyl or (3–8C) cycloalkyl which may bear one or more substituents selected from the group consisting of halo, (3–6C) cycloalkyl, cyano, nitro, hydroxy, (1–4C))alkoxy, (1–5C))alkanoyloxy, aroyl, heteroaroyl, oxo, imino (which may bear a (1–6C)alkyl, (3–6C)cycloalkyl, (1–5C)alkanoyl or aroyl substituent), hydroxyimino (which hydroxyimino may bear a (1–4C))alkyl or a phenyl substituent on the oxygen), an amino group of formula NR$^{ga}$R$^{gb}$, an amino group of formula NR$^{gc}$R$^{gd}$, an amidino group of formula C(=NR$^{gg}$)NR$^{ge}$R$^{gf}$, and a carbamoyl group of formula CON(OR$^{gh}$)R$^{gi}$, but excluding any radical wherein a hydroxy and an oxo substituent together form a carboxy group, wherein an amino group of formula NR$^{ga}$R$^{gb}$ contains zero to seven carbon atoms and each of R$^{ga}$ and R$^{gb}$ is independently hydrogen, (1–5C)alkyl or (3–6C)cycloalkyl, or the radical NR$^{ga}$R$^{gb}$ is pyrrolidino, piperidino, morpholino, thiomorpholino (or its S-oxide) or piperazinyl (which piperazinyl may bear a (1–3C)alkyl substituent group at the 4-position); and wherein R$^{gc}$ is hydrogen or (1–3C)alkyl and R$^{gd}$ is (1–5C)alkanoyl, aroyl or heteroaroyl; or R$^{gd}$ is a group of formula C(=J$^g$)NR$^{ge}$R$^{gf}$ in which J$^g$ is oxygen, sulfur, NR$^{gg}$ or CHR$^{gj}$; and wherein the amino group NR$^{ge}$R$^{gf}$ contains zero to seven carbon atoms and each of R$^{ge}$ and R$^{gf}$ is independently hydrogen, (1–5C)alkyl or (3–6C)cycloalkyl, or the radical NR$^{ge}$R$^{gf}$ is pyrrolidino, piperidino, morpholino, thiomorpholino (or its S-oxide) or piperazinyl (which piperazinyl may bear a (1–3C)alkyl substituent at the 4position) or R$^{ge}$ is hydrogen or 1–4C)alkyl and R$^{gf}$ together with R$^{gg}$ forms an ethylene or trimethylene group; R$^{gg}$ is hydrogen, (1–4C)alkyl or together with R$^{gf}$ forms an ethylene or trimethylene group; R$^{gj}$ is cyano, nitro or SO$_2$R$^{gk}$ and R$^{gk}$ is 1–4C)alkyl or phenyl; R$^{gh}$ and R$^{gi}$ are independently (1–3C)alkyl; and in which a cyclic group which is a substituent on Z$^g$ or formed by substitution on Z$^g$ may bear one or more (1–3C)alkyl groups on carbon as further substituents; and in which any aryl or heteroaryl group which is a part of the group Z$^g$ may bear one or more halo, (1–4C)alkyl, (1–4C)alkoxy, cyano, trifluoromethyl or nitro substituents;

for a radical of formula Ih, G$^h$ denotes a single bond, a double bond or a divalent hydrocarbon radical; J$^h$ denotes a radical joined to the ring by a single bond if G denotes a double bond or, otherwise, a radical joined by a double bond; M$^h$ denotes a heteroatom, a substituted heteroatom, or a single bond; and L$^h$ denotes a hydrocarbon radical in which the 1-position is attached to M$^h$; wherein the values of G$^h$, j$^h$, M$^h$ and L$^h$ are selected from (a) G$^h$ is a single bond; J$^h$ is oxo or thioxo; M$^h$ is oxy, thio or NR$^{ha}$; and L$^h$ is L$^{ha}$;

(b) G$^h$ is a single bond; J$^h$ is NR$^{hb}$; M$^h$ is NR$^{ha}$; and L$^h$ is L$^{ha}$;

(c) G$^h$ is a double bond, J$^h$ is OR$^{ha}$, SR$^{ha}$ or NR$^{hc}$R$^{hd}$; M$^h$ is nitrogen; and L$^h$ is L$^{ha}$;

(d) G$^h$ is methylene which may bear one or two methyl substituents; J$^h$ is oxo, thioxo or NR$^{he}$; M$^h$ is oxy, thio, sulfinyl, sulfonyl or NR$^{ha}$; and L$^h$ is L$^{hb}$;

(e) G$^h$ is a single bond; J$^h$ is oxo, thioxo or NR$^{he}$; M$^h$ is nitrogen; and L$^h$ is L$^{hc}$;

(f) G$^h$ is methine, which may bear a (1–3C)alkyl substituent; J$^h$ is oxo, thioxo or NR$^{he}$; M$^h$ is nitrogen; and L$^h$ is L$^{hd}$; (g) G$^h$ is cis-vinylene, which may bear one or two methyl substituents; J$^h$ is oxo, thioxo, or NR$^{he}$; M$^h$ is nitrogen; and L$^h$ is L$^{he}$; and (h) G$^h$ is a single bond; J$^h$ is oxo or thioxo; M$^h$ is a single bond; and L$^h$ is L$^{hf}$; wherein R$^{ha}$ is hydrogen or (1–3C)alkyl; R$^{hb}$ is hydrogen, (1–3C)alkyl, cyano, (1–3C)alkylsulfonyl or nitro; R$^{hc}$ and R$^{hd}$ are independently hydrogen or (1–3C)alkyl or the radical NR$^{hc}$R$^{hd}$ is pyrrolidino, piperidino, morpholino, thiomorpholino (or its S-oxide) or piperazinyl (which piperazinyl may bear a (1–3C)alkyl substituent at the 4-position); R$^{he}$ is hydrogen or (1–3C)alkyl; L$^{ha}$ is ethylene, cis-vinylene, trimethylene or tetramethylene which radical L$^{ha}$ itself may bear one or two methyl substituents; L$^{hb}$ is ethylene or trimethylene which radical L$^{hb}$ itself may bear one or two methyl substituents; L$^{hc}$ is prop-2-en-1-yliden-3-yl, which radical L$^{hc}$ itself may bear one or two methyl substituents; L$^{hd}$ is cis-vinylene, which radical L$^{hd}$ itself may bear one or two methyl substituents; L$^{he}$ is methine, which radical L$^{he}$ itself may bear a (1–3C)alkyl substituent; and L$^{hf}$; is 4-oxabutan-1,4-diyl;

for a radical of formula Ij, X$^j$ is (1–6C)alkyl, -CH$_2$R$^{ja}$, —CH$_2$SR$^{ja}$, —CH$_2$S(O)R$^{jg}$, —CH$_2$S(O)$_2$R$^{jg}$, —COR$^{ja}$, —COOR$^{ja}$, C(=J$^{ja}$)NR$^{jb}$R$^{jc}$, —C(R$^{ja}$)(OR$^{jd}$)(OR$^{je}$), —CH$_2$N(R$^{ja}$)C(=J$^{ja}$)R$^{jf}$, —CH$_2$N(R$^{ja}$)COOR$^{jg}$ or —CH$_2$N(R$^{ja}$)C(=J$^{ja}$)NR$^{jb}$R$^{jc}$;

B$^j$ is a direct bond and L$^j$ is a hydrocarbon chain in which the 1-position is bound to B$^j$ and L$^j$ is selected from trimethylene, tetramethylene, cis-1-butenylene and cis, cis-butadienylene; or B$^j$ is N(R$^{jh}$) and L$^h$ is a hydrocarbon chain selected from ethylene, trimethylene and cis-vinylene; or B$^j$ is N and L$^j$ is a hydrocarbon chain in which the 1-position is bound to B$^j$ and L$^j$ is cis,cis-prop-2-en-1-ylidin-3-yl; J$^j$ and J$^{ja}$ are independently oxygen or sulfur; R$^{ja}$, R$^{jf}$ and R$^{jh}$ are independently hydrogen or (1–6C)alkyl; R$^{jb}$ and R$^{jc}$, are independently hydrogen or (1–6C)alkyl; or the radical NR$^{jb}$R$^{jc}$, is pyrrolidino, piperidino, morpholino, thiomorpholino (or its S-oxide) or piperazinyl (which piperazinyl may bear a (1–3C)alkyl substituent at the 4-position); R$^{jd}$ and R$^{je}$ are independently (1–3C)alkyl or together form a divalent hydrocarbon chain selected from ethylene and trimethylene; R$^{jg}$ is (1–6C)alkyl;

for a radical of formula Ik, Z$^k$ is a nitrogen linked radical of formula II wherein E$^1$, E$^2$, E$^3$ and E$^4$ form a divalent four membered chain (—E$^1$=E$^2$—E$^3$=E$^4$—) in which each of E$^1$, E$^2$, E$^3$ and E$^4$ is methine; or in which one or two of E$^1$, E$^2$, E$^3$ and E$^4$ is nitrogen and the remaining E$^1$, E$^2$, E$^3$ and E$^4$ are methine; and further wherein one or more of E$^1$, E$^2$, E$^3$ and E$^4$ which is methine may bear a halo, (1–3C)alkyl, hydroxy, (1–3C)alkoxy, (1–3C)alkylthio, (1–3C)alkylsulfinyl or (1–3C)alkylsulfonyl substituent; and wherein the radicals F$^k$, G$^k$, and I$^k$(X$^k$) are selected from (a) G$^k$ is a direct bond, I$^k$(X$^k$) is a radical having the formula =C(Z$^k$)— and F$^k$ is a radical selected from —CH= and —N=;

(b) G$^k$ is a direct bond, I$^k$(X$^k$) is a radical having the formula —C(=J$^k$)— and F$^k$ is a radical selected from —N(R$^{kf}$)—, —CH$_2$—CH$_2$—, —CH=CH—, —CH$_2$—N(R$^{kf}$)— and —CH=N—;

(c) G$^k$ is a radical having the formula —CH$_2$—, I$^k$(X$^k$) is a radical having formula —C(=J$^k$)— and F$^k$ is selected from —CH$_2$— and —N(R$^{kf}$)—; and (d) G$^k$ is selected from —CH$_2$—, —CH$_2$—CH$_2$—, —CH=CH— and —N=CH—, I$^k$(X$^k$) is a radical having the formula —C(=J$^k$) and F$^k$ is a direct bond; wherein J$^k$ is oxygen or sulfur; Z$^k$ is —OR$^{ka}$, —SR$^{ka}$, —COR$^{ka}$, —COOR$^{ka}$, —C(=J$^{ka}$) NR$^{kb}$R$^{kc}$ or —C(R$^{ka}$)(OR$^{kd}$)(OR$^{ke}$); J$^{ka}$ is oxygen or sulfur; R$^{ka}$ and R$^{kf}$ are independently hydrogen or (1–6C)alkyl; R$^{kb}$ and R$^{kc}$ are independently hydrogen or (1–6C)alkyl; or the radical NR$^{kb}$R$^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimido, and 3-oxa-, 3-thia- and 3-azaglutarimido, in which the imido radical may bear one or more (1–3C)alkyl substituents and, in addition, the aromatic portion of the phthalimido may bear one or more halo, hydroxy or (1–3C)alkoxy substituents; and for a radical of formula Im, $R^{ma}$ and $R^{mb}$ are independantly selected from the group consisting of hydrogen, (1–3C)alkyl, (3–6C)cycloalkyl, phenyl, benzyl, and phenethyl; and $R^{mc}$ is pyrrolidino, piperidino, morpholino, thiomorpholino (or its S-oxide), piperazinyl (which piperazinyl may bear a (1–3C)alkyl substituent at the 4-position); or $R^{mc}$ is —$NR^{md}R^{me}$, wherein $R^{md}$ and $R^{me}$ are independently selected from hydrogen, (1–3C)alkyl, phenyl, benzyl and phenethyl; and wherein for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C)alkoxy, methylenedioxy, hydroxy, mercapto, —S(O)$_n R^{xa}$, (1–5C)alkanoyl, (1–5C)alkanoyloxy, nitro, $NR^{xb}R^{xc}$, $NR^{xd}R^{xe}$, C(=$NR^{xf}$)$NR^{xg}R^{xh}$, $CONR^{xb}R^{xc}$ and $COOR^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical $NR^{xb}R^{xc}$ contains zero to seven carbons and each of $R^{xb}$ and $R^{xc}$ is independently hydrogen, (1–5C)alkyl or (3–6C)cycloalkyl, or the radical $NR^{xb}R^{xc}$ is pyrrolidino, piperidino, morpholino, thiomorpholine (or its S-oxide) or piperazinyl (which piperazinyl may bear a (1–3C)alkyl substituent at the 4position); and wherein $R^{xd}$ is hydrogen or (1–4C)) alkyl and $R^{xe}$ is (1–5C)alkanoyl, benzoyl; or a group of formula C(=$J^x$)$NR^{xg}R^{xh}$ in which $J^x$ is oxygen, sulfur, $NR^{xf}$ or $CHR^{xi}$; $R^{xf}$ is hydrogen, (1–5C)alkyl or together with $R^{xg}$ forms an ethylene or trimethylene diradical, the radical $NR^{xg}R^{xh}$ contains zero to 7 carbons and each of $R^{xg}$ and $R^{xh}$ is independently hydrogen, (1–5C)alkyl or (3–6C)cycloalkyl, or the radical $NR^{xg}R^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C))alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

$Q^2$ is a group B or $CH_2B$ wherein B is phenyl which may bear one or two substituents independently selected from halo, trifluoromethyl, hydroxy, (1–3C)alkoxy, (1–3C)alkyl and methylenedioxy; or B is thienyl, imidazolyl, benzo[b]thiophenyl or naphthyl any of which may bear a halo substituent; or B is biphenylyl; or B is carbon-linked indolyl which may bear a benzyl substituent at the 1-position;

$Q^3$ is hydrogen, or 1–4C)alkyl; and $Q^4$ is a radical selected from —OC(=O)$NR^3R^4$, —N($R^6$)C(=O)$OR^2$, —N($R^6$)C(=O)$NR^3R^4$, —N($R^6$)C(=O)$SR^5$, —SC(=O)$NR^3R^4$, —N($R^6$)C(=O)$R^{15}$, and wherein $R^2$ and $R^5$ are independently (1–6C)alkyl, (3–7C)cycloalkyl, aryl, heteroaryl, aryl(1–3C)alkyl, heteroaryl(1–3C)alkyl or a radical of formula XV, wherein any aryl or heteroaryl group or radical of formula XV may bear one, two or three substituents independently selected from halo, trifluoromethyl, hydroxy, (1–3C)alkoxy, (1–3C)alkyl, cyano, —$NR^7R^8$, C(=O)$NR^9R^{10}$, —S(=O)$NR^{11}R^{12}$, —S(=O)$_2 N^{11}R^{12}$, and methylenedioxy, and further wherein any arylethyl, arylpropyl, heteroarylethyl or heteroarylpropyl group may optionally be substituted at the position a to the aryl or heteroaryl group by a group selected from oxo, and =$NOR^{13}$;

$R^3$ and $R^4$ are independently selected from hydrogen, (1–6C)alkyl, (3–7C)cycloalkyl, aryl, heteroaryl, aryl(1–3C)alkyl, heteroaryl(1–3C)alkyl, and a radical of formula XV, wherein any aryl or heteroaryl group, or radical of formula XV may bear one two or three substituents independently selected from halo, trifluoromethyl, hydroxy, (1–3C)alkoxy, (1–3C)alkyl, cyano, —$NR^7R^8$, C(=O)$NR^9R^{10}$, —S(=O)$NR^{11}R^{12}$, —S(=O)$_2NR^{11}R^{12}$, and methylenedioxy, and further wherein any arylethyl, arylpropyl, heteroarylethyl or heteroarylpropyl group may optionally be substituted at the position a to the aryl or heteroaryl group by a group selected from oxo, and =$NOR^{13}$; or —$NR^3R^4$ taken together represents a cyclic amino radical selected from pyrrolidinyl, piperidino, 1,2,3,6-tetrahydro-pyridyl, 1,2,3,4-tetrahydroquinolyl, 1,2,3,4-tetrahydroisoquinolyl, which cyclic amino radical may bear one or two substituents independently selected from halo, trifluoromethyl, hydroxy, (1–3C)alkoxy, (1–3C)alkyl, cyano, —$NR^7R^8$, —C(=O)$NR^9R^{10}$, —S(=O)$NR^{11}R^{12}$, —S(=O)$_2NR^{11}R^{12}$, phenyl, acetamidomethyl, and methylenedioxy;

$R^{15}$ and $R^{16}$ are independently (1–6C)alkyl, (3–7C)cycloalkyl, aryl, heteroaryl, aryl(1–3C)alkyl, heteroaryl(1–3C)alkyl, or a radical of formula XV, wherein any aryl or heteroaryl group or radical of formula XV may bear one, two or three substituents independently selected from halo, trifluoromethyl, hydroxy, (1–3C)alkoxy, (1–3C)alkyl, cyano, —$NR^7R^8$, C(=O)$NR^9R^{10}$, —S(=O)$NR^{11}R^{12}$, —S(=O)$_2NR^{11}R^{12}$, and methylenedioxy, E is selected from —O—, —S—, —N($R^{14}$)—, —S(=O)— and —S(O)$_2$—;

m is 1, 2, or 3; and $R^6$–$R^{14}$ are independently selected from hydrogen and (1–3C)alkyl;

or the N-oxide of a piperidino nitrogen in $Q^1$;

or a pharmaceutically acceptable salt thereof;

or a quaternary ammonium salt thereof in which the piperidino nitrogen in $Q^1$ is a quadricovalent ammonium nitrogen wherein the fourth radical on the nitrogen $R^1$ is 1–4C)alkyl or benzyl and the associated counterion A is a pharmaceutically acceptable anion;

provided that the compound of formula I is not N-phenyl-1-(2,4-dichlorophenyl)-3-piperidinopropyl carbamate, N-phenyl-1-(4-methylphenyl)-3-piperidinopropyl carbamate, N-(1-isopropyl-1-naphthyl-3-piperidinopropyl)ethyl carbamate, N-phenyl-1-phenyl-3-piperidinopropyl carbamate, N-phenyl-1-phenyl-3-pyrrolidinopropyl carbamate, N-ethyl-1-phenyl-3-piperidinopropyl carbamate, or N-phenyl-1-(4-propoxyphenyl)-3-piperidinopropyl carbamate.

A preferred sub-set of compounds of the invention are compounds of formula I wherein:

$Q^1$ is selected from radicals of formulae Ia, Ib, Ic, Id, Ie, If, Ig, Ih, Ij and Ik; and $Q^4$ is a radical selected from —OC(=O)NR$^3$R$^4$, —N(R$^6$)C(=O)OR$^2$, —N(R$^6$)C(=O)NR$^3$R$^4$, —N(R$^6$)C(=O)SR$^5$, and —SC(=O)NR$^3$R$^4$;

$R^2$ and $R^5$ are independently (1–6C)alkyl, (3–7C)cycloalkyl, aryl, heteroaryl, aryl(1–3C)alkyl, or heteroaryl(1–3C)alkyl, wherein any aryl or heteroaryl group may bear one, two or three substituents independently selected from halo, trifluoromethyl, hydroxy, (1–3C)alkoxy, (1–3C)alkyl, cyano, —NR$^7$R$^8$, C(=O)NR$^9$R$^{10}$, —S(=O)NR$^{11}$R$^{12}$, —S(=O)$_2$NR$^{11}$R$^{12}$, and methylenedioxy, and further wherein any arylethyl, arylpropyl, heteroarylethyl or heteroarylpropyl group may optionally be substituted at the position a to the aryl or heteroaryl group by a group selected from oxo, and =NOR$^{13}$; and m is 1 or 2;

or the N-oxide of a piperidino nitrogen in $Q^1$;

or a pharmaceutically acceptable salt thereof;

or a quaternary ammonium salt thereof in which the piperidino nitrogen in $Q^1$ is a quadricovalent ammonium nitrogen wherein the fourth radical on the nitrogen $R^1$ is 1–4C)alkyl or benzyl and the associated counterion A is a pharmaceutically acceptable anion.

Another preferred sub-set of compounds of the invention are compounds of formula I wherein:

$Q^1$ is 4-acetamido4-phenylpiperidino, 4-(2-methylsulfinylphenyl)piperidino, 4-(2-oxopiperidino)piperidino, or 4-(2-oxoperhydropyrimidin-1-yl)piperidino;

$Q^2$ is a group B or —CH$_2$B wherein B is phenyl which may bear one or two substituents independently selected from halo, trifluoromethyl, hydroxy, (1–3C) alkoxy, (1–3C)alkyl and methylenedioxy; or B is thienyl, imidazolyl, benzo[b]thiophenyl or naphthyl any of which may bear a halo substituent; or B is biphenylyl; or B is carbon-linked indolyl which may bear a benzyl substituent at the 1-position;

$Q^3$ is hydrogen; and $Q^4$ is a radical selected from —OC(=O)NR$^3$R$^4$, —N(R$^6$)C(=O)OR$^2$, —N(R$^6$)C(=O)NR$^3$R$^4$, —N(R$^6$)C(=O)SR$^5$, and —SC(=O)NR$^3$R$^4$; wherein $R^2$ and $R^5$ are independently (1–6C)alkyl, (3–7C)cycloalkyl, aryl, heteroaryl, aryl(1–3C)alkyl or heteroaryl(1–3C)alkyl, wherein any aryl or heteroaryl group may bear one, two or three substituents independently selected from halo, trifluoromethyl, hydroxy, (1–3C)alkoxy, (1–3C)alkyl, cyano, —NR$^7$R$^8$, C(=O)NR$^9$R$^{10}$, —S(=O)NR$^{11}$R$^{12}$, and methylenedioxy;

$R^3$ and $R^4$ are independently selected from hydrogen, (1–6C)allyl, (3–7C)cycloalkyl, aryl, heteroaryl, aryl(1–3C)alkyl, heteroaryl(1–3C)alkyl, and a radical of formula XV, wherein any aryl or heteroaryl group, or radical of formula XV may bear one two or three substituents independently selected from halo, trifluoromethyl, hydroxy, (1–3C)alkoxy, (1–3C)alkyl, cyano, —NR$^7$R$^8$, C(=O)NR$^9$R$^{10}$, —S(=O)NR$^{11}$R$^{12}$, —S(=O)$_2$NR$^{11}$R$^{12}$, methylenedioxy; or —NR$^3$R$^4$ taken together represents a cyclic amino radical selected from pyrrolidinyl, piperidino, 1,2,3,6-tetrahydro-pyridyl, 1,2,3,4-tetrahydroquinolyl, 1,2,3,4-tetrahydroisoquinolyl, which cyclic amino radical may bear one or two substituents independently selected from halo, trifluoromethyl, hydroxy, (1–3C)alkoxy, (1–3C)alkyl, cyano, —NR$^7$R$^8$, —C(=O)NR$^9$R$^{10}$, —S(=O)NR$^{11}$R$^{12}$, —S(=O)$_2$NR$^{11}$R$^{12}$, phenyl, acetamidomethyl, and methylenedioxy;

E is —O—;

m is 1 or 2; and $R^6$–$R^{12}$ and $R^{14}$ are independently selected from hydrogen and (1–3C)alkyl;

or the N-oxide of a piperidino nitrogen in $Q^1$;

or a pharmaceutically acceptable salt thereof;

or a quaternary ammonium salt thereof in which the piperidino nitrogen in $Q^1$ is a quadricovalent ammonium nitrogen wherein the fourth radical on the nitrogen $R^1$ is (1–4C)alkyl or benzyl and the associated counterion A is a pharmaceutically acceptable anion.

It will be appreciated that a compound of formula I may contain one or more asymmetically substituted carbon atoms and that such a compound may be isolated in optically active, racemic and/or diastereomeric forms. A compound may exhibit polymorphism. It is to be understood that the present invention encompasses any racemic, optically-active, diastereomeric, polymorphic or stereoisomeric form, or mixture thereof, which form possesses NK1 and NK2 antagonist properties, it being well known in the art how to prepare optically-active forms (for example, by resolution of the racemic form or by synthesis from optically-active starting materials) and how to determine the NK1 and NK2 antagonist properties by the standard tests known in the art and those described hereinafter. It may be preferred to use the compound of formula I in a form which is characterized as containing, for example, at least 95%, 98% or 99% enantiomeric excess of the form which is of the (S)-configuration at the center indicated by * in formula I.

In this specification $R^1$, $R^2$, et cetera stand for generic radicals and have no other significance. It is to be understood that the generic terms "(1–3C)alkyl" and "(1–6C)alkyl" include both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms, consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

Particular values listed below for radicals, substituents and ranges are for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl, imidazolyl, indolyl or pyrimidinyl. A particular value for halo is chloro or bromo. A particular value for (1–3C)alkyl is methyl, ethyl, propyl or isopropyl; for 1–4C) alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C)cycloalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for 1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrmidinyl which ring may be unsubstituted or may bear a methoxy, hydroxy or methylsulfinyl substituent. A more particular value for heteroaryl is pyridyl; halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cycloalkyl is cyclopropyl or cyclopentyl; for (3–7C) cycloalkyl is cyclopropyl or cyclopentyl; and for (3–8C) cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular value for $Q^1$ is 4-hydroxy-4-phenylpiperidino, 4-acetamido4-phenylpiperidino, 4-(2-methylsulfinylphenyl)piperidino, 4-(2-oxopiperidino)-piperidino, or 4-(2-oxoperhydropyrimidin-1-yl)piperidino; for $Q^2$ is 3,4-dichlorophenyl, or 3,4-methylenedioxyphenyl; for $Q^3$ is hydrogen; and for $Q^4$ is N-benzylcarbamoyloxy, N-[(S)-α-methylbenzyl]carbamoyloxy, 3-methyl-3-(2-methoxybenzyl)ureido, phenethylcarbonyloxy, 3-indan-1-ylureido, 2-methoxyphenethylcarbonylamino, and 2-methoxybenzyloxy-carbonylamino.

A more particular value for $Q^1$ is 4-acetamido-4-phenylpiperidino.

A more particular value for $Q^4$ is N-benzylcarbamoyloxy, N-[(S)-α-methylbenzyl]carbamoyloxy, and 3-methyl-3-(2-methoxybenzyl)ureido,.

A particular value for $Q^2$ is 3,4-dichlorophenyl, or 3,4-methylenedioxyphenyl.

A particular value for E is —O—.

A particular group of compounds of formula I are compounds wherein $Q^1$ is selected from radicals of formulae Ia, Ib, Ic, Ie, If, Ig, Ih, Ij, Ik, and Im.

A particular group of compounds of formula I are compounds wherein $Q^1$ is selected from radicals of formulae Ia, Ic, Ie, If, Ig, Ih, Ij, Ik, and Im.

A particular group of compounds of formula I are compounds wherein $Q^1$ is selected from radicals of formulae Ia, Ib, Ic, Ie, If, Ig, Ih, Ij and Ik.

A particular group of compounds of formula I are compounds wherein $Q^1$ is selected from radicals of formulae Ie, If, Ig, Ih, Ij Ik and Im.

A particular group of compounds of formula I are compounds wherein $Q^1$ is selected from radicals of formulae Ie, If, Ig, Ih, Ij and Ik.

A particular group of compounds of formula I are compounds wherein $Q^1$ is a radical of formula Ia.

A particular group of compounds of formula I are compounds wherein $Q^1$ is a radical of formula Ib.

A particular group of compounds of formula I are compounds wherein $Q^1$ is a radical of formula Ic.

A particular group of compounds of formula I are compounds wherein $Q^1$ is a radical of formula Id.

A particular group of compounds of formula I are compounds wherein $Q^1$ is a radical of formula Ie.

A particular group of compounds of formula I are compounds wherein $Q^1$ is a radical of formula If.

A particular group of compounds of formula I are compounds wherein Q I is a radical of formula Ig.

A particular group of compounds of formula I are compounds wherein $Q^1$ is a radical of formula Ih.

A particular group of compounds of formula I are compounds wherein Q is a radical of formula Ij.

A particular group of compounds of formula I are compounds wherein $Q^1$ is a radical of formula Ik.

A particular group of compounds of formula I are compounds wherein $Q^1$ is a radical of formula Im.

A particular group of compounds are compounds of formula I wherein $Q^1$ is a radical of formula Ib wherein $Z^b$ is a disubstituted methylene group $R^{bb}(CH_2)_p$—C—$R^{bc}$.

A particular group of compounds of formula I are compounds wherein $Q^4$ is —OC(=O)NR$^3$R$^4$.

A particular group of compounds of formula I are compounds wherein $Q^4$ is —N(R$^6$)C(=O)OR$^2$.

A particular group of compounds of formula I are compounds wherein $Q^4$ is —N(R$^6$)C(=O)NR$^3$R$^4$.

A particular group of compounds of formula I are compounds wherein $Q^4$ is —N(R$^6$)C(=O)SR$^5$.

A particular group of compounds of formula I are compounds wherein $Q^4$ is —SC(=O)NR$^3$R$^4$.

A particular group of compounds of formula I are compounds wherein $Q^4$ is, —N(R$^6$)C(=O)R$^{15}$.

A particular group of compounds of formula I are compounds wherein $Q^4$ is —OC(=O)R$^{16}$.

A particular group of compounds of formula I are compounds wherein $R^2$, $R^3$, $R^4$ and $R^5$ are independently selected from (1–6C)alkyl and (3–7C)cycloalkyl.

A particular group of compounds of formula I are compounds wherein $R^2$, $R^3$, $R^4$ and $R^5$ are independently selected from aryl, heteroaryl, aryl(1–3C)alkyl or heteroaryl (1–3C)alkyl, wherein any aryl or heteroaryl group may bear one, two or three substituents independently selected from halo, trifluoromethyl, hydroxy, (1–3C)alkoxy, (1–3C)alkyl, cyano, —NR$^7$R$^8$, C(=O)NR$^9$R$^{10}$, —S(=O)NR$^{11}$R$^{12}$, —S(=O)$_2$NR$^{11}$R$^{12}$, and methylenedioxy.

A more particular group of compounds of formula I are compounds of formula III wherein $Q^1$ is selected from radicals of formulae Ie, If, Ig, Ih, Ij, Ik and Im.

A more particular group of compounds of formula I are compounds of formula III wherein $Q^1$ is selected from radicals of formulae Ie, If, Ig, Ih, Ij and Ik.

A more particular group of compounds of formula I are compounds of formula III wherein $Q^4$ is, —OC(=O)NR$^3$R$^4$.

A more particular group of compounds of formula I are compounds of formula III wherein $Q^4$ is —N(R$^6$)C(=O)OR$^2$.

A more particular group of compounds of formula I are compounds of formula III wherein $Q^4$ is —N(R$^6$)C(=O)NR$^3$R$^4$.

A more particular group of compounds of formula I are compounds of formula III wherein $Q^4$ is —N(R$^6$)C(=O)SR$^5$.

A more particular group of compounds of formula I are compounds of formula III wherein $Q^4$ is —SC(=O)NR$^3$R$^4$.

A more particular group of compounds of formula I are compounds of formula III wherein $Q^4$ is, —N(R$^6$)C(=O)R$^{15}$.

A more particular group of compounds of formula I are compounds of formula III wherein $Q^4$ is —OC(=O)R$^{16}$.

Pharmaceutically acceptable salts of a compound of formula I include those made with a strong inorganic or organic acid which affords a physiologically acceptable anion, such as, for example, hydrochloric, sulfuric, phosphoric, methanesulfonic, or para-toluenesulfonic acid.

A compound of formula I may be made by processes which include processes known in the chemical art for the production of structurally analogous heterocyclic compounds. Such processes for the manufacture of a compound of formula I as defined above are provided as further features of the invention and are illustrated by the following procedures in which the meanings of generic radicals are as defined above unless otherwise indicated:

(a) For a compound of formula I wherein $Q^4$ is an oxygen linked radical —OC(=O)NR$^3$R$^4$, reacting an alcohol of formula VII with a suitable isocyanate of formula OCNR$^3$R$^4$, under standard conditions. The reaction may conveniently be carried out, for example, using conditions similar to those described in Example 1.

(b) Alkylating an amine of formula Q$^1$H with an aldehyde of formula XIV by reductive alkylation. The alkylation may conveniently be carried out by the in situ acid-catalyzed formation of an imminium salt, followed by reduction with a suitable reducing agent such as for example sodium cyanoborohydride in alcoholic solvent.

(c) For an acid addition salt of a compound of formula I, treating a corresponding compound of formula I which is in the free-base form, with an acid. The salt may conveniently be formed in a suitable solvent, such as for example diethyl ether, benzene or toluene.

(d) For an N-oxide of a piperidino nitrogen in Q$^1$, oxidizing the piperidino nitrogen of a corresponding compound of formula I using a conventional procedure, such as, for example, using hydrogen peroxide in methanol, peracetic acid, 3-chloroperoxybenzoic acid in an inert solvent (such as dichloromethane) or dioxirane in acetone.

(e) For a quaternary ammonium salt of the piperidino nitrogen in Q$^1$, alkylating the piperidino nitrogen in a corresponding compound of formula I with an alkylating agent of formula R$^1$Z wherein Z is a leaving group, such as for example, a chloro, bromo, iodo, tosyl, brosyl, mesyl or trifyl group.

(f) For a compound of formula I which bears a sulfinyl group, oxidizing the sulfur of a corresponding compound of formula I which bears a sulfide group using a conventional method.

(g) For a compound of formula I which bears a sulfonyl group, oxidizing a sulfide or sulfinyl group of a corresponding compound of formula I using a conventional method.

(h) For a compound of formula I which bears an aromatic hydroxy group, cleaving the ether of a corresponding compound of formula I which bears an aromatic alkoxy group using a conventional method.

(i) For a compound of formula I wherein $Q^4$ is an oxygen linked radical —OC(=O)R$^{16}$, reacting an alcohol of formula VII with a suitable acid chloride of formula ClC(=O) R$^{16}$ or an equivalent activated acid derivative, under standard conditions. The reaction may conveniently be carried out, for example, using conditions similar to those described in Example 41.

(j) For a compound of formula I wherein $Q^4$ is an oxygen linked radical —NC(=O)R$^{15}$, reacting an amine of formula IX with a suitable acid chloride of formula ClC(=O) R$^{15}$ or an equivalent activated acid derivative, under standard conditions.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. The reagents and reaction conditions for such procedures are well known in the chemical art.

If not commercially available, the necessary starting materials for the above procedures may be made by procedures which are selected from standard techniques of organic chemistry, techniques which are analogous to the synthesis of known, structurally similar compounds and techniques which are analogous to the above described procedures or the procedures described in the Examples. As will be clear to one skilled in the art, a variety of sequences are available for the preparation of the starting materials, and the sequences leading to the starting materials and products of the invention may be altered if appropriate considerations regarding the synthetic methods and radicals present are followed. The starting materials, intermediates and the procedures for their preparation are additional aspects of the invention. Intermediates of formula VII, AX, or XIV, wherein the radicals Q1, Q2, Q3, Q4, etc. have any of the values, particular values, or more particular values listed herein above, are particularly useful for preparing compounds of the invention.

An alcohol of formula VII may be prepared from a hydrochloride salt of formula Q$^1$H.HCl as shown in Scheme I. Treatment with aqueous formaldehyde followed by acetic anhydride gives a transient hemi-aminal intermediate of formula IV, which can be treated directly with a ketone of formula V to give a ketone of formula VI. Reduction of the keytone VI, for example, using sodium borohydride, yields the desired alcohol.

An amine of formula IX may be prepared from a ketone of formula VI as shown in Scheme II. Conversion of the ketone to an imide of formula VIII followed by reduction of the imide using standard conditions such as for example, reduction with diimide, gives the desired amine of formula IX. As shown in Scheme II, an amine of formula IX may also be prepared directly from an alcohol of formula VII using standard conditions, such as for example, by treatment with triphenylphosphine and diethyl azodicarboxlate. An amine of formula IX may also be prepared from an alcohol of formula VII via a phthalimido compound of formula X as shown in Scheme II. Conversion of the alcohol functionality to a suitable leaving group, followed by displacement with a phthalimido nucleophile, gives a compound of formula X, which may be converted to an amine of formula IX using standard conditions.

An aldehyde of formula XIV wherein $Q^4$ is a nitrogen linked radical, can be prepared as outlined in Scheme III. An acid of formula XI may be converted to an iso-cyanate of formula XII under standard conditions, such as for example by treatment with diphenylphosphoryl azide and triethylamine in toluene at 100° C. The iso-cyanate can be converted to an alkene of formula XIII by treatment with a nucleophyle (Y) of formula $—OR^2$, $—SR^5$ or $—NH(R^3)$ ($R^4$), using standard conditions. Oxidative cleavage of the alkene gives an aldehyde of formula XIV, wherein $Q^4$ is a nitrogen linked radical. The oxidative cleavage may conveniently be carried out under standard conditions, such as for example by treatment with sodium periodate and osmium tetroxide in tetrahydrofuran and water.

The utility of a compound of the invention or a pharmaceutically acceptable salt thereof (hereinafter, collectively referred to as a "Compound") may be demonstrated by standard tests and clinical studies, including those disclosed in the publications noted above, and those described below.
SP Receptor Binding Assay (Test A)

The ability of a Compound of the invention to antagonize the binding of SP at the NK1 receptor may be demonstrated using an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.*, 1991, 180, 1110–1117; and the NK1 receptor was expressed in Mouse Erythroleukemia (MEL) cells using a procedure similar to that described in Test B below.
Neurokinin A (NKA) Receptor Binding Assay (Test B)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19. In an initial use of this assay, the $IC_{50}$ measured for the standard compound L-659,877 was found to be 30 nM versus $^3$H-NKA binding to MEL-membranes.

The selectivity of a Compound for binding at the NK1 and the NK2 receptors may be shown by determining its binding at other receptors using standard assays, for example, one using a tritiated derivative of NKB in a tissue preparation selective for NK3 receptors. In general, the Compounds of the invention which were tested demonstrated statistically significant binding activity in Test A and Test B with a $K_i$ of 1 mM or much less typically being measured. For example, the compound of Example 1 demonstrated a Ki of 163 nanomolar in Test A, and a Ki of 6.81 nanomolar in Test B.

Rabbit Pulmonary Artery: NK1 in vitro Functional Assay (Test C)

The ability of a Compound of the invention to antagonize the action of the agonist Ac-[$Arg^6$, $Sar^9$, $Met(O_2)^{11}$] Substance P (6–11), ASMSP, in a pulmonary tissue may be demonstrated as follows.

Male New Zealand white rabbits are euthanized via i.v. injection into the ear vein with 60 mg/kg Nembutal (50 mg/ml). Preceding the Nembutal into the vein is Heparin (1000 units/mil) at 0.0025 ml/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs. The segments are suspended between stainless steel stirrups, so as not to remove any of the endothelium, and placed in water-jacketed (37° C.) tissue baths containing physiological salt solution of the following composition (mM): NaCl, 118.0; KCl, 4.7; $CaCl2$, 1.8; $MgCl_2$, 0.54; $NaH_2PO_4$, 1.0; $NaHCO_3$, 25.0; glucose, 11.0; indomethacin, 0.005(to inhibit cyclooxygenase); and dl-Propranolol, 0.001(to block β receptors); gassed continuously with 95% $O_2$-5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1\times10^{-6}$M Thiorphan (to block E.C.3.4.24.11), $3\times10^{-8}$M (S)-N-[2-(3,4-Dichloro-phenyl)4-[4(2-oxoperhydropyrimidin-1-yl)piperidino]butyl]-N-methylbenzamide (to block $NK_2$ receptors), and the given concentration of the Compound being tested. At the end of the 1.0 hour equilibration, $3\times10^{-6}$M Phenylephrine hydrochloride is added for 1.0 hour. At the end of the 1.0 hour, a dose relaxation curve to ASMSP is done. Each tissue is treated as a individual and is considered finish when it fails to relax further for 2 consecutive doses. When a tissue is complete, $1\times10^{-3}$M Papaverine is added for maximum relaxation.

Percent inhibition is determined when a tested Compound produces a statistically significant (p<0.05) reduction of the total relaxation which is calculated using the total relaxation of the Papaverine as 100%. Potencies of the Compounds are determined by calculating the apparent dissociation constants ($K_4$B) for each concentration tested using the standard equation:

$$K_B=[\text{antagonist}]/(\text{dose ratio}-1)$$

where dose ratio=antilog[(agonist −log molar $EC_{50}$ without Compound)−(−log molar $EC_{50}$ with Compound)]. The $K_B$ values may be converted to the negative logarithms and expressed as −log molar $K_B$ (i.e. $pK_B$). For this evaluation, complete concentration-response curves for agonist obtained in the absence and presence of the Compound tested using paired pulmonary artery rings. The potency of the agonist is determined at 50% of its own maximum relaxation in each curve. The $EC_{50}$ values are converted to negative logarithms and expressed as −log molar $EC_{50}$.
NK2 in vitro Functional Assay (Test D)

The ability of a Compound of the invention to antagonize the action of the agonist [β-$ala^8$]NKA (4–10), BANK, in a pulmonary tissue may be demonstrated as follows.

Male New Zealand white rabbits are euthanized via i.v. injection into the ear vein with 60 mg/kg Nembutal (50 mg/ml). Preceding the Nembutal into the vein is Heparin (1000 units/ml) at 0.0025 ml/kg for anticoagulant purposes.

The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; and indomethacin, 0.005 (to inhibit cyclooxygenase); gassed continuously with 95% $O_2$-5% $CO_2$. Responses are measured on a Grass polygraph via Grass FT-03 transducers.

Initial tension placed on each tissue is 2 grams, which is maintained throughout the 45 minute equilibration period. Tissues are washed with the physiological salt solution at 15 minute intervals. After the 45 minute equilibration period, $3 \times 10^{-2}$M KCl is given for 60 minutes to test the viability of the tissues. The tissues are then washed extensively for 30 minutes. The concentration of the Compound being tested is then added for 30 minutes. At the end of the 30 minutes, a cumulative dose response curve to BANK is performed. Each tissue is treated as a individual and is considered finish when it fails to contract further for 2 consecutive doses. When a tissue is complete, $3 \times 10^{-2}$M $BaCl_2$ is added for maximum contraction.

Percent inhibition is determined when a tested Compound produces a statistically significant (p<0.05) reduction of the total contraction which is calculated using the total contraction of the $BaCl_2$ as 100%. Potencies of the Compounds are determined by calculating the apparent dissociation constants ($K_B$) for each concentration tested using the standard equation:

$$K_B = [\text{antagonist}]/(\text{dose ratio} - 1)$$

where dose ratio=antilog[(agonist −log molar $EC_{50}$ without Compound)−(−log molar $EC_{50}$ with Compound)]. The $K_B$ values may be converted to the negative logarithms and expressed as −log molar $K_B$ (i.e. $pK_B$). For this evaluation, complete concentration-response curves for agonist obtained in the absence and presence of the Compound tested using paired pulmonary artery rings. The potency of the agonist is determined at 50% of its own maximum relaxation in each curve. The $EC_{50}$ values are converted to negative logarithms and expressed as −log molar $EC_{50}$.

$NK_1$ and $NK_2$ in vivo Functional Assay (Test E)

The activity of a compound as an antagonist of NK1 and/or NK2 receptors also may be demonstrated in vivo in laboratory animals as described in: Buckner et al. "Differential Blockade by Tachykinin NK1 and NK2 Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exo. Ther.,* 1993, Vol 267(3), pp 1168–1175. The assay is carried out as follows.

Compounds are tested in anesthetized guinea pigs pretreated with i.v. indomethacin (10 mg/kg, 20 min.), propranolol (0.5 mg/kg, 15 min.), and thiorphan (10 mg/kg, 10 min). Antagonists or vehicle are administered i.v. and orally, 30 and 120 minutes prior to increasing concentrations of agonist, respectively. The agonists used in these studies are ASMSP (Ac-[$Arg^6$,$Sar^9$,Met($O_2$)$^{11}$]-SP(6–11) and BANK (β-ala-8 NKA4-10). Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm (−$logED_{50}$). Data are expressed as mean±SEM and statistical differences were determined using ANOVA/Tukey-Kramer and Student's t-test , with p<0.05 considered statistically significant.

Clinical Studies

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in the above described Tests is not limited to asthma, but rather, that the Tests provide evidence of general antagonism of both SP and NKA.

SP and NKA have been implicated in the pathology of numerous diseases including: rheumatoid arthritis, Alzheimer's disease, oedema, allergic rhinitis, inflammation pain, gastrointestinal-hypermotility, anxiety, emesis, Huntington's Disease, Psycoses, hypertension, migraine, bladder hypermotility and uticaria Accordingly, one feature of the invention is the use of a compound of formula I or a pharmaceutically acceptable salt thereof in the treatment of a disease in a human or other mammal in need thereof in which SP or NKA is implicated and antagonism of its action is desired.

Asthma is characterized by both chronic inflammation and hyperresponsiveness of the airways. The NK1 receptor is known to mediate inflammation and mucus hypersecretion in airways; and the NK2 receptor is involved in the control of the tone of bronchial smooth muscle. Thus, agents capable of antagonizing the actions of SP and NKA, at the NK1 and NK2 receptors, respectively, are capable of reducing both the chronic inflammation and the airway hyperresponsiveness which are symptomatic of asthma. It has been suggested that an antagonist having mixed affinity for NK1 and NK2 could be therapeutically superior to a receptor selective antagonist. C. M. Maggi "Tachykinin Receptors and Airway Pathophysiology" *EUR. Respir. J.,* 1993, 6, 735–742 at 739. Also, it has been suggested that a synergistic effect against bronchoconstriction may result from the simultaneous application of an NK1 antagonist and an NK2 antagonist. D. M. Foulon, et al. "NK1 and NK2 Receptors Mediated Tachykinin and Resiniferatoxin-induced Bronchospasm in Guinea Pigs" *American Review of Respiratory Disease,* 1993, 148, 915–921. Accordingly, another feature of the invention is the use of a compound of formula I or a pharmaceutically acceptable salt thereof in the treatment of asthma in a human or other mammal in need thereof.

Because of the range of effects attributable to the actions of SP and NKA, compounds which are capable of blocking their actions may also be useful as tools for further evaluating the biological actions of other neurotransmitters in the Tachykinin family. As a result, another feature of the invention is provided by the use of a compound of formula I or a salt thereof as a pharmacological standard for the development and standardization of new disease models or assays for use in developing new therapeutic agents for treating diseases in which SP or NKA are implicated or for assays for their diagnosis.

When used in the treatment of a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) Mass spectra (MS) were run using an automated system with atmospheric pressure chemical ionization (APCI). Methanol mobile phase enters the probe were it is pneumatically converted into an aerosol and rapidly heated into the gas phase at the probe tip. Hot gas from the probe enters the heated volume of the source which contains the corona discharge pin typically maintained at 3 kV. Methanol molecules rapidly react with ions from the corona discharge to produce stable reagent ions. Analyte molecules introduced into the mobile phase react with the reagent ions at atmospheric pressure and typically become protonated (for positive ions) or deprotonated (for negative ions). Where indicated, the following alternative methods of ionization were used; a) desorption chemical ionization (CI) using methane reagent gas and a direct exposure probe; b) electron impact (EI) or c) fast atom bombardment (FAB). Generally, only spectra where parent masses are observed are reported.

EXAMPLE 1

N-Benzyl-3-(4-acetamido4-phenylpiperidino)-1-(3, 4-dichlorophenyl)propyl carbamate Benzylisocyanate (25 uL) was added to the alcohol from b below (75 mg), in tetrahydrofuran (1.0 mL). After 2 hours, additional benzylisocyanate (5 microliters), was added and the mixture stirred for 1 hour. The solvents were evaporated and the residue purified by chromatography, with methanol-:dichloromethane (5:95) as the eluent, to give the title compound as a white foam (63 mg); MS (APCI) m+H+554. Analysis for $C_{30}H_{33}N_3O_3Cl_2$. 0.25 $H_2O$: Calculated: C, 64.46; H, 6.04; N, 7.52; Found: C, 64.24, H, 5.99, N; 7.52.

The intermediate alcohol was prepared as follows.

a. 3-(4-Acetamido-4-phenylpiperidino)-1-(3,4-dichlorophenyl)propanone hydrochloride salt. Hydrochloric acid (1.32 mL, 6.25 N) was added to 4-acetamido-4-phenyl-piperidine. (1.73 g). Formalin (0.525 mL) was added and the resulting solution was allowed to stir overnight. Acetic anhydride (3.4 mL) was added and the solution was heated to reflux for 75 minutes. 3,4-dichloroacetophenone was added and the mixture was allowed to reflux overnight. The solvent was evaporated and the residual solid was suspended in acetone, collected by filtration, rinsed with acetone, and dried in vacuo to afford the ketone as the hydrochloride salt (2.52 g). This material was used directly in sub-part b, without further purification.

b. 3-(4-Acetamido-4-phenylpiperidino)-1-(3,4-dichlorophenyl)-1-propanol. The ketone from sub-part a (530 mg) was suspended in ethanol (4 mL). An equal volume of tetrahydrofuran was added, followed by sodium borohydride (100 mg). After 4 hours, water was added and the solvent was evaporated. The residue was partitioned between diethyl ether and water. The ether phase was washed (saturated brine), dried (anhydrous sodium sulfate), filtered, and evaporated to give an oil. Chromatography, with dichloromethane:methanol (20:1) as the eluent gave the alcohol as a white foam (0.31 g).

EXAMPLE 2

N-((S)-a-Methylbenzyl)-3-(4-acetamido4-phenylpiperidino)-1-(3,4-dichlorophenyl) propyl carbamate Using a procedure similar to that described in Example 1, except replacing the benzylisocyanate used therein with (S)-(–)-a-methylbenzyl isocyanate, the title compound was prepared; MS (APCI) m+H=568.

EXAMPLE 3

N-(2-Methoxybenzyl)-N-methyl-N-'-[1-(S)-(3,4-dichlorophenyl)-3-(4-(2-(S)-methylsulfinylphenyl)-piperidino)propyl]urea.

The aldehyde from sub-part b below (0.250 g) was dissolved in tetrahydrofuran (1 mL). 4-(2-(S)-Methylsulfinylphenyl)piperidine (0.169 g) was added followed by acetic acid (0.055 g). Methanol (8 mL) was added followed by sodium cyanoborohydride (0.051 g). After 4 hours the mixture was concentrated and the residue partitioned between ethyl acetate (50 mL) and saturated aqueous $NaHCO_3$ (20 mL). The organic phase was separated, extracted with brine (20 mL), dried ($Na_2SO_4$), filtered, and evaporated. The residue was purified by chromatography with dichloromethane:methanol (95:5) as the eluent to give the title compound as a white solid (0.175 g). MS(APCI): m+H=602. Analysis for $C_{31}H_{37}Cl_2N_3O_3S.0.5\ H_2O$: Calculated: C, 60.88; H, 6.26; N, 6.87; Found: C, 61.05; H, 6.27; N, 7.14;

The intermediate N-(2-Methoxybenzyl)-N-methyl-N'-[1-(S)-(3,4-dichlorophenyl)-3-oxopropyl]urea was prepared as follows.

a. N-(2-Methoxybenzyl)-N-methyl-N'-[1-(S)-(3,4-dichlorophenyl)-3-butenyl]urea. 2-(S)-(3,4-dichlorophenyl)-4-pentenoic acid (1.22 g) was dissolved in toluene (60 mL) under nitrogen. Triethylamine (0.51 g) was added followed by diphenylphosphoryl azide (1.38 g). The mixture was heated at 100° C. for 16 hours, cooled to room temperature, and N-methyl-2-methoxybenylamine (1.00 g) was added. After 2 hours the reaction was diluted with HCl (50 mL, 1N) and ethyl acetate (50 mL). The organic phase was separated, and extracted with saturated aqueous $NaHCO_3$ (25 mL), and with brine (25 mL). The organic phase was dried ($Na_2SO_4$), filtered and evaporated. The residue was purified by chromatography with hexane-:ethyl acetate (4:1) as the eluent to afford the urea as a yellow oil (1.40 g). MS(APCI): m+H=393.

b. N-(2-Methoxybenzyl)-N-methyl-N'-[1-(S)-(3,4-dichlorophenyl)-3-oxopropyl]urea. The material from sub-part a above (1.39 g) was dissolved in tetrahydrofuran (30 mL) and water (10 mL). Osmium tetroxide (0.01 g) was added. Sodium periodate (1.63 g) was added gradually in portions over 10 minutes. After 3 hours the reaction was diluted with water (20 mL) and saturated aqueous NaHCO3(20 mL), and extracted with ethyl ether (3×50 mL). The combined organic extracts were washed with brine (50 mL), dried ($Na_2SO_4$), filtered, and evaporated. The residue was purified by filtration through a florisil plug, to give the aldehyde as a colorless oil (0.75 g). MS(APCI): m+H= 395.

The intermediate 4-(2-(S)-methylsulfinylphenyl) piperidine was prepared as described in International Patent Application Publication Number WO 95/16682, Example 68, sub-parts a and b. The absolute configuration of the sulfoxide center is (S).

EXAMPLES 4–5

Using a procedure similar to that described in Example 3, except replacing the 4-(2-methylsulfinylphenyl)piperidine used therein with the requsite piperidine, the following compounds of formula I wherein $Q^2$ is 3,4-dichlorophenyl, $Q^3$ is hydrogen, $Q^4$ is 3-(2-methoxybenzyl)-3-methylureido and $Q^1$ has the indicated value were prepared. The compounds of Examples 4 and 5 were prepared as the (S) enantiomer at the center marked by * in formula I.

EXAMPLE 4

$Q^1$=4-Acetamido-4-phenylpiperidino; MS(APCI): m+H= 597.

Analysis for $C_{32}H_{38}Cl_2N_4O_3$. 0.4 $H_2O$: Calculated: C, 63.55; H, 6.47; N, 9.26; Found: C, 63.64; H, 6.47; N, 9.22.

EXAMPLE 5

$Q^1$=4(2-(Oxoperhydropyrimidinyl)-piperidino; MS(APCI): m+H=562. Analysis for $C_{28}H_{37}Cl_2N_5O_3.0.4\ H_2O$: Calculated: C, 59.03; H, 6.69; N, 12,29; Found: C, 59.01; H, 6.61; N, 12.26.

EXAMPLES 6–13

Using a procedure similar to that described in Example 3, except replacing the 4-(2-methylsulfinylphenyl)piperidine used therein with the requsite piperidine, the following compounds of formula I wherein $Q^2$ is 3,4-dichlorophenyl, $Q^3$ is hydrogen, $Q^4$ is 3-indan-1-ylureido and $Q^1$ has the indicated value were prepared. The compounds were prepared as the (S) enantiomer at the center marked by * in formula I.

EXAMPLE 6

$Q^1$=4-Hydroxy-4-phenylpiperidino; MS(APCI): m+H= 538.

EXAMPLE 7

$Q^1$=4-Carbamoyl-4-piperidinopiperidino; MS(APCI): m+H=572

EXAMPLE 8

$Q^1$=4-(2-Oxopiperidino)-4-(N-methylcarbamoyl) piperidino; MS(APCI): m+H=600

EXAMPLE 9

$Q^1$=4-(2-Oxopiperidino)piperidino; MS(APCI): m+H= 543

EXAMPLE 10

$Q^1$=4-(2-(S)-methylsulfinylphenyl)piperidino; MS(APCI): m+H=584

EXAMPLE 11

$Q^1$=4-(2-Oxo-2,3-dihydrobenzimidazol-1-yl)piperidino; MS(APCI): m+H=578

EXAMPLE 12

$Q^1$=4-Acetamido-4-phenylpiperidino; MS(APCI): m+H=579

EXAMPLE 13

$Q^1$=4-(4-Methylsulfinylphenyl)piperidino; MS(APCI): m+H=584.

The intermediate (S)-3-(3,4-dichlorophenyl)-3-(3-indan-1-ylureido)propanal, used to prepare the compounds of Examples 6–13, was prepared using a sequence similar to that described in Example 3, sub-parts a and b, by substituting 1-aminoindan for N-methyl-2-methoxybenzylamine in sub-part a; MS(APCI): m+H=377.

EXAMPLES 14–20

Using a procedure similar to that described in Example 3, except replacing the 4-(2-methylsulfinylphenyl)piperidine used therein with the requsite piperidine, the following compounds of formula I wherein $Q^2$ is 3,4-dichlorophenyl, $Q^3$ is hydrogen, Q4 is 3-(2-methoxybenzyl)-3-methylureido and $Q^1$ has the indicated value were prepared. The compounds were prepared as the (S) enantiomer at the center marked by * in formula I.

EXAMPLE 14

$Q^1$=4-Carbamoyl-4-(dimethylamino)piperidino; MS(APCI): m+H=550.

EXAMPLE 15

$Q^1$=4-Carbamoyl-4-piperidinopiperidino; MS(APCI): m+H=590.

EXAMPLE 16

$Q^1$=4-(2-Oxopiperidino)-4-(N-methylcarbamoyl)piperidino; MS(APCI): m+H=618

EXAMPLE 17

$Q^1$=4-(2-Oxopiperidino)piperidino; MS(APCI): m+H=561

EXAMPLE 18

$Q^1$=4-(4-Methylsulfinylphenyl)piperidino; MS(APCI): m+H=602

EXAMPLE 19

$Q^1$=4(2-Oxo-2,3-dihydrobenzimidazol-1-yl)piperidino; MS(APCI): m+H=596.

EXAMPLE 20

$Q^1$=4-Hydroxy-4-phenylpiperidino; MS(APCI): m+H=556.

EXAMPLES 21–30

Using a procedure similar to that described in Example 3, except replacing the 4-(2-methylsulfinylphenyl)piperidine used therein with the requsite piperidine, the following compounds of formula I wherein $Q^2$ is 3,4-dichlorophenyl, $Q^3$ is hydrogen, Q is 2-methoxyphenethylcarbonylamino and $Q^1$ has the indicated value were prepared. The compounds were prepared as the (S) enantiomer at the center marked by * in formula I.

EXAMPLE 21

$Q^1$=4-Hydroxy-4-phenylpiperidino; MS(APCI): m+H=541.

EXAMPLE 22

$Q^1$=4-Carbamoyl-4-(dimethylamino)piperidino; MS(APCI): m+H=535.

EXAMPLE 23

$Q^1$=4-Carbamoyl-4-piperidinopiperidino; MS(APCI): m+H=575.

EXAMPLE 24

$Q^1$=4-(2-Oxopiperidino)4-(N-methylcarbamoyl)piperidino; MS(APCI): m+H=603.

EXAMPLE 25

$Q^1$=4-(2-Oxopiperidino)piperidino; MS(APCI): m+H=546.

EXAMPLE 26

$Q^1$=4-(4-Methylsulfinylphenyl)piperidino; MS(APCI): m+H=587.

EXAMPLE 27

$Q^1$=4-(2-(S)-Methylsulfinylphenyl)piperidino; MS(APCI): m+H=587.

EXAMPLE 28

$Q^1$=4-(2-Oxo-2,3-dihydrobenzimidazol-1-yl)piperidino; MS(APCI): m+H=581.

EXAMPLE 29

$Q^1$=4-(2-Oxoperhydropyrimidin-1-yl)piperidino; MS(APCI): m+H=547.

EXAMPLE 30

$Q^1$=4-Acetamido4-phenylpiperidino; MS(APCI): m+H=582.

The intermediate (S)-3-(3,4-dichlorophenyl)-3-(2-methoxyphenethylcarbonylamino) propanal, used to prepare the compounds of Examples 21–30 was prepared as follows.

a. (S)-4-(3,4-Dichlorophenyl)-4-(tert-butoxycarbonylamino)-1-butene. (S)-2-(3,4-dichlorophenyl)-4-pentenoic acid (5.00 g) was dissolved in 2-methyl-2-propanol (75 mL) under nitrogen. Diphenylphosphoryl azide (5.61 g) was added followed by triethylamine (2.06 g). The reaction mixture was heated at 60° C. for 1 hour, and at 80° C. for 48 hours. The mixture was cooled to room temperature, diluted with water (150 mL), and extracted with ethyl acetate (3×150 mL). The organic extracts were combined, washed with aqueous HCl (100 ML, 1N), saturated aqueous NaHCO$_3$ (100 mL), and brine (100 mL). The organic phase was dried (Na$_2$SO$_4$), filtered and evaporated to afford the tert-butyl carbamate as a colorless oil (4.12 g); MS(APCI): (m+H=316).

b. (S)4(3,4-dichlorophenyl)-4-(2-methoxyphenethylcarbonylamino)-1-butene. The material from sub-part a above was dissolved in dicloromethane (25 mL), cooled to 20° C., and trifluoroacetic acid (20 mL) was added dropwise. After 30 minutes the mixture was evaporated. The resulting red oil was dissolved in dichloromethane (5 mL) and added to a dicloromethane (50 mL) solution of 3-(2-methoxyphenyl)propionyl chloride at 0° C. under nitrogen, and triethylamine (3.00 g) was added. The reaction mixture was stirred overnight at room temperature, diluted with ether (150 mL) and extracted with aqueous HCl (100 mL, 1N), saturated aqueous NaHCO$_3$ (100 mL), and brine (100 mL). The organic phase was dried (Na$_2$SO$_4$), filtered and evaporated. The residue was purified by chromatography with hexane:ethyl acetate (4:1) as the eluent to give the amide (3.26 g); MS(APCI): m+H=378.

c. (S)-3-(3,4-dichlorophenyl)-3-(2-methoxyphenethylcarbonylamino)propanal. The material from sub-part b above (3.00 g) was dissolved in tetrahydrofuran (75 mL) and water (10 mL). Osmium tetroxide (0.02 g) was added. Sodium periodate (3.54 g) was added gradually in portions over 20 minutes. After 3 hours the reaction was diluted with water (100 mL), and extracted with ethyl ether (3×150 mL). The combined organic extracts were washed (aqueous NaHCO$_3$, brine), dried (Na$_2$SO$_4$), filtered, and evaporated. The residue was purified by chromatography with hexane:ethyl acetate (2:1) as the eluent to give the aldehyde (2.10 g); MS(APCI): m+H=380.

EXAMPLES 31–40

Using a procedure similar to that described in Example 3, except replacing the 4-(2-methylsulfinylphenyl)piperidine used therein with the requsite piperidine, the following compounds of formula I wherein $Q^2$ is 3,4-dichlorophenyl, $Q^3$ is hydrogen, $Q^4$ is 2-methoxybenzyloxycarbonylamino and $Q^1$ has the indicated value were prepared. The compounds were prepared as the (S) enantiomer at the center marked by * in formula I.

EXAMPLE 31

$Q^1$=4-Hydroxy-4 phenylpiperidino; MS(APCI): m+H=543.

EXAMPLE 32

$Q^1$=4-Carbamoyl4-(dimethylamino)piperidino; MS(APCI): m+H=537.

EXAMPLE 33

$Q^1$=4—Carbamoyl-4-piperidinopiperidino; MS(APCI): m+H=577.

EXAMPLE 34

$Q^1$=4-(2-Oxopiperidino)-4-(N-methylcarbamoyl)piperidino; MS(APCI): m+H=605.

EXAMPLE 35

$Q^1$4-(2-Oxopiperidino)piperidino; MS(APCI): m+H=548.

EXAMPLE 36

$Q^1$=4-(4-Methylsulfinylphenyl)piperidino; MS(APCI): m+H=589.

EXAMPLE 37

$Q^1$=4-(2-(S)-Methylsulfinylphenyl)piperidino; MS(APCI): m+H=589.

EXAMPLE 38

$Q^1$=4-(2-Oxo-2,3-dihydrobenzimidazol-1-yl)piperidino; MS(APCI): m+H=583.

EXAMPLE 39

$Q^1$=4-(2-Oxoperhydropyrimidin-1-yl)piperidino; MS(APCI): m+H=549.

EXAMPLE 40

$Q^1$=4-Acetamido-4-phenylpiperidino; MS(APCI): m+H=584.

The intermediate is (S)-3-(3,4-dichlorophenyl-3-(2-methoxybenzyloxycarbonylamino)propanal, used to prepare the compounds of Examples 31–40 was prepared as follows.

a. (S)-4-(3,4-dichlorophenyl)-4-(2-methoxybenzyloxycarbonylamino)-1-butene-2-(S)-(3,4-dichlorophenyl)-4-pentenoic acid (1.22 g) was dissolved in toluene (100 mL) under nitrogen. Diphenylphosphoryl azide (5.61 g) was added followed by triethylamine (2.06 g). The mixture was kept at room temperature for 30 minutes, heated at 60° C. for 1 hour, and heated at 80° C. for 2 hours. The mixture was cooled to room temperature, 2-Methoxybenzyl alcohol (5.63 g) was added, and the mixture was heated at 80° C. for 72 hours. The mixture was cooled and diluted with water (100 mL) and ethyl acetate (100 mL). The organic phase was separated, and the aqueous phase extracted with additional ethyl acetate (2×100 mL). The combined organic extracts were washed with aqueous HCl (100 mL, 1N), saturated aqueous NaHCO$_3$ (100 mL), and with brine (100 mL). The organic phase was dried (Na$_2$SO$_4$), filtered and evaporated. The residue was purified by crystallization from ether-hexane to give the carbamate as a white solid (6.15 g); MS(APCI): m+H=380.

b. (S)-3-(3,4-Dichlorophenyl-3-(2-methoxybenzyloxycarbonylamino)propanal. The material from sub-part a above (6.05 g) was dissolved in tetrahydrofuran (75 mL) and water (25 mL). Osmium tetroxide (0.04 g) was added. Sodium periodate (7.15 g) was added gradually in portions over 20 minutes. After 3 hours the reaction was diluted with water (100 mL) and extracted with ether (3×150 mL). The combined organic extracts were washed with saturated aqueous NaHCO$_3$ (150 mL), and brine (150 mL), dried (Na$_2$SO$_4$), filtered, and evaporated. The residue was purified by filtration through a florisil plug, to give the aldehyde as a foamy solid (5.22 g); MS(APCI): m+H=382.

EXAMPLE 41

3-(4-Acetamido-4-phenylpiperidino)-1-(3,4-dichlorophenyl)propyl3-phenylpropionate 3-Phenylpropionylchloride (21 mg) and triethylamine (13 mg) were added to the alcohol (50 mg) from Example 1 sub-part b in dichloromethane (3 mL) under nitrogen. The mixture was stirred 2 hours at room temperature, and was diluted with saturated aqueous NaHCO$_3$ (10 mL) and ethyl acetate (10 mL). The organic phase was separated, washed with brine (5 mL), dried (Na$_2$SO$_4$), filtered and evaporated. The resulting yellow oil was converted to its hydrochloride salt by treating a dichloromethane (5 mL) solution with dry hydrogen chloride (0.2 mL×1N in ether) for 10 minutes at room temperature. Evaporation gave a solid which was purified by trituration with ether to give the title compound as a white solid (40 mg); MS(APCI): m+H=553.

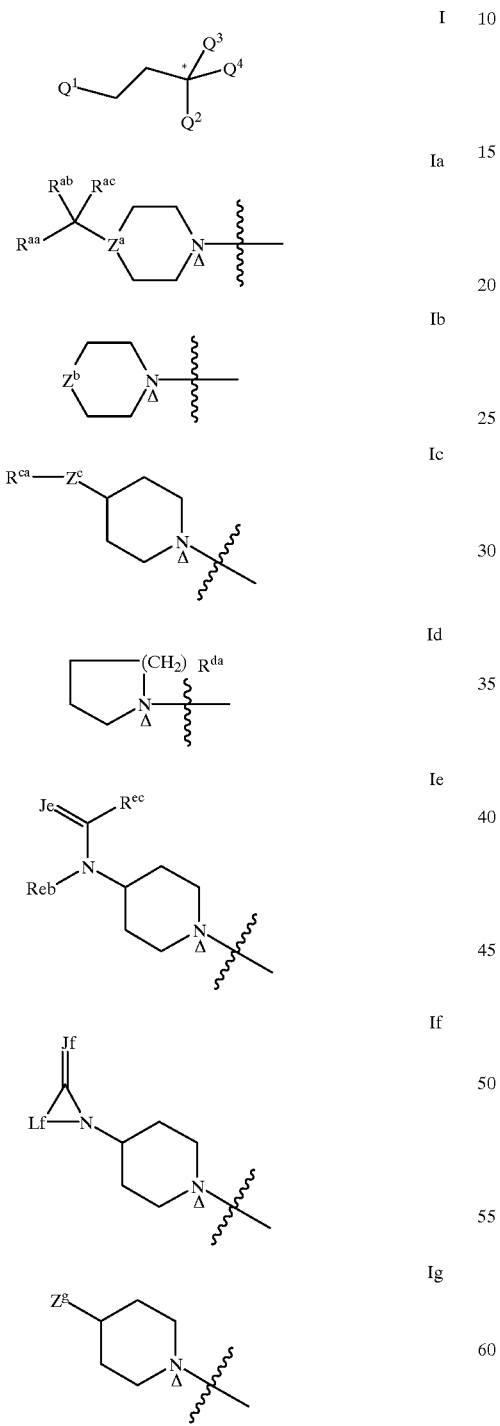

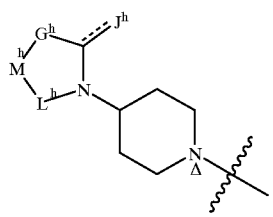

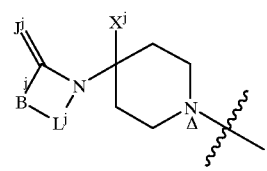

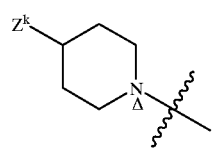

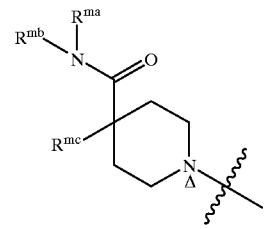

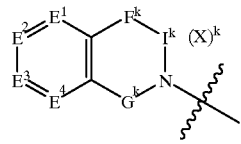

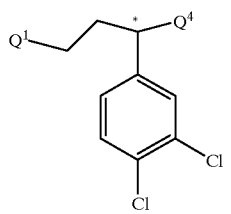

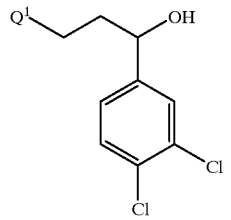

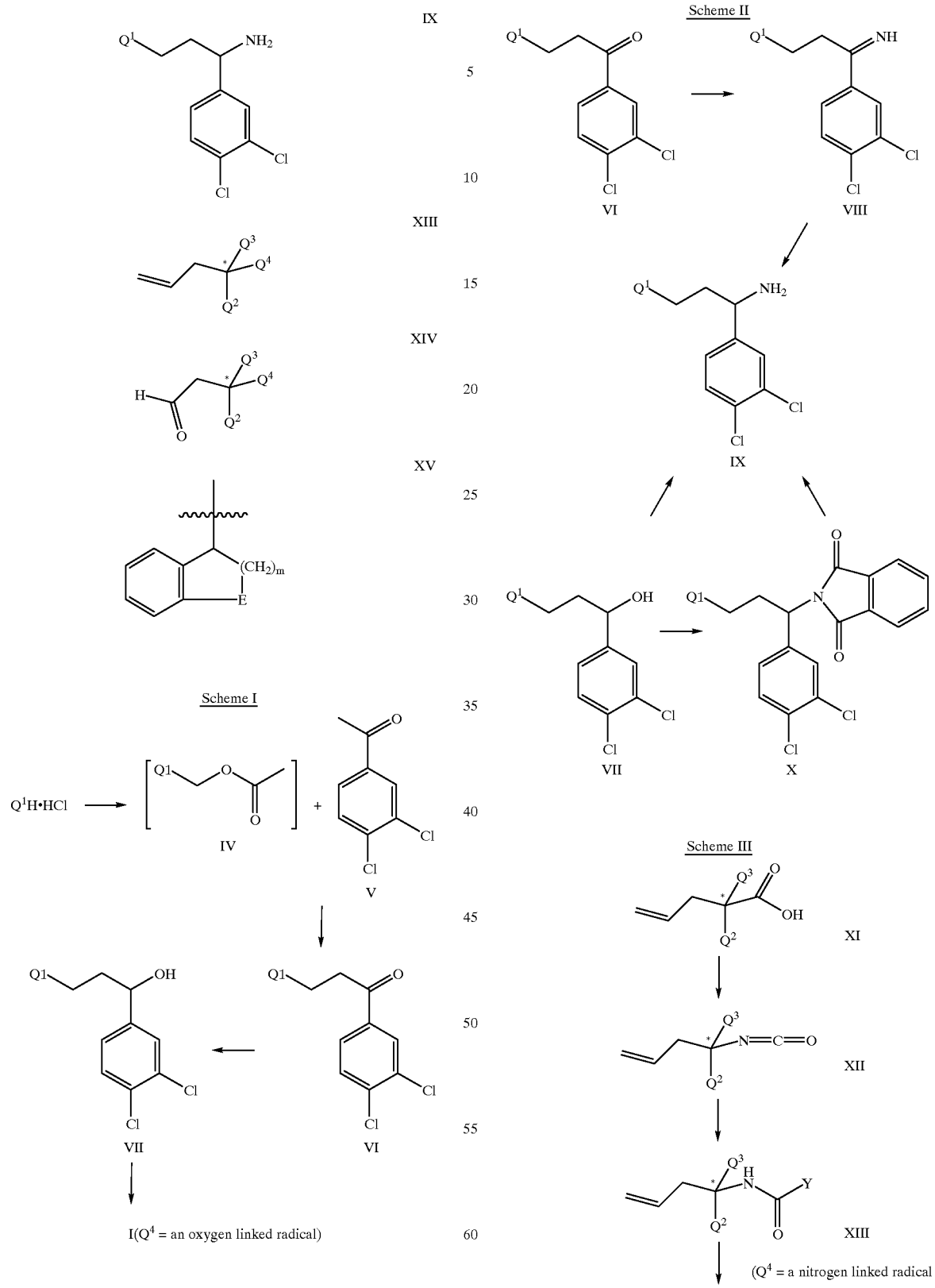

-continued

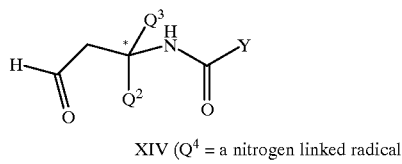

XIV (Q⁴ = a nitrogen linked radical)

What is claimed is:

1. A compound of formula XVI:

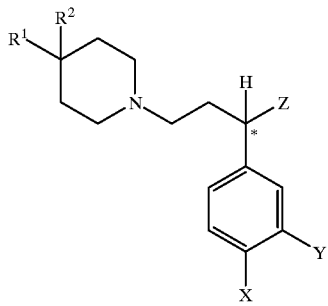

(XVI)

wherein $R^1$ is independently selected from the group consisting of hydroxy, dimethylamino, acetamido, phenyl, methyl-sulphinyl-phenyl, 2-oxo-perhydro-pyrimidinyl, piperidino, 2-oxo-piperidino, carbamoyl, N-methyl-carbamoyl, and 2-oxo-2,3-dihydro-benzimidazolyl;

$R^2$ is independently selected from the group consisting of H, hydroxy, dimethylamino, acetamido, phenyl, methyl-sulphinyl-phenyl, 2-oxo-perhydro-pyrimidinyl, piperidino, 2-oxo-piperidino, carbamoyl, N-methyl-carbamoyl, and 2-oxo-2,3-dihydro-benzimidazolyl;

X and Y are independently selected from the group consisting of H, halogen, and hydroxy, provided that X or Y is halogen;

Z is selected from the group consisting of —OC(=O)NR³₂, —N(R⁴)C(=O)OR³, —N(R⁴)C(=O)NR³₂, —N(R⁴)C(=O)SR³, —SC(=O)NR³₂, —N(R⁴)C(=O)R³, and —OC(=O)R³; wherein $R^3$ at each occurrence is independently selected from the group consisting of $C_1$–$C_6$-alkyl, $C_3$–$C_7$-cycloalkyl, aryl, heteroaryl, aryl-$C_1$–$C_3$-alkyl, heteroaryl-$C_1$–$C_3$-alkyl, and a radical of formula XV,

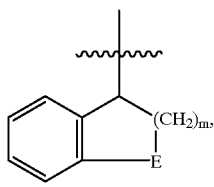

(XV)

where any aryl or heteroaryl group or radical of $R^3$ may be mono-, di- or tri-substituted with substituents independently selected from the group consisting of halo, trifluoromethyl, hydroxy, $C_1$–$C_3$-alkoxy, $C_1$–$C_3$-alkyl, cyano, and methylenedioxy, and further wherein any arylethyl, arylpropyl, heteroarylethyl or heteroarylpropyl group may be substituted at the position α to the aryl or heteroaryl group by an oxo group; and where, in a radical of formula XV, E is selected from —O—, —S—, —N(R³)—, —S(=O)— and —SO₂—; m is 1, 2, or 3; and $R^3$ is as heretofore defined;

$R^4$ at each occurrence is independently selected from hydrogen or $C_1$–$C_3$-alkyl;

or, any of the foregoing compounds having an N-oxide at the piperidino nitrogen in formula XVI;

or, a pharmaceutically-acceptable salt of any of the foregoing compounds.

2. A compound according to claim 1, wherein X is halogen.

3. A compound according to claim 2, wherein X is chloro.

4. A compound according to claim 1, wherein $R^1$ and $R^2$ are independently selected from the group consisting of hydrogen, acetamido, phenyl, 2-oxoperhydropyrimidinyl, hydroxy, carbamoyl, piperidino, 2-oxopiperidino, 4-methylsulfinylphenyl, N-methylcarbamoyl, 2-oxo-2,3-dihydrobenzimidazol-1-yl, 2-(S)-methylsulfinyl and dimethylamino.

5. A compound according to claim 4, wherein:

$R^1$ is selected from the group consisting of acetamido, 2-oxoperhydropyrimidinyl, hydroxy, carbamoyl, 2-oxopiperidino, 2-(S)-methylsulfinyl, 2-oxo-2,3-dihydrobenzimidazol-1-yl, and 4-methylsulfinylphenyl; and $R^2$ is independently selected from the group consisting of hydrogen, phenyl, piperidino, N-methylcarbamoyl, and dimethylamino.

6. A compound according to claim 1, selected from the group consisting of N-benzyl-3-(4-acetamido-4-phenylpiperidino)-1-(3,4-dichlorophenyl)propyl carbamate, N-((S)-(α-methylbenzyl)-3-(4-acetamido-4phenylpiperidino)-1-(3,4-dichlorophenyl)propyl-carbamate, N-(2-methoxybenzyl)-N-methyl-N'-[-1-(S)-(3,4-dichlorophenyl)-3-(4-(2-(S)-methylsulfinylphenyl)-piperidino) propyl]urea, and 3-(4-acetamido-4-phenylpiperidino)-1-(3,4-dichlorophenyl)propyl 3-phenylpropionate.

7. A compound according to claim 1, having NK1- and NK2-receptor antagonist properties, in an optically-active, racemic, diastereomeric, polymorphic or stereoisomeric form, or any mixture thereof.

8. A compound according to claim 1, comprising an enantiomeric excess of the form which has an (S)-configuration at the center indicated by * in formula XVI.

9. A pharmaceutical composition comprising a pharmaceutically-acceptable excipient or diluent; and any compound according to claim 1, or an N-oxide, or a pharmaceutically-acceptable salt of any compound according to claim 1.

10. A method of treating a condition in a human or other mammal in which SP or NKA is implicated and antagonism of its action is desired, said method comprising:

administering a physiologically-effective amount of any compound according to claim 1; or administering a physiologically-effective amount of an N-oxide, or a pharmaceutically-acceptable salt of any compound according to claim 1.

11. The method of claim 10, wherein the condition is asthma in a human or other mammal suffering therefrom.

12. A compound according to claim 6, having NK1- and NK2-receptor antagonist properties, in an optically-active, racemic, diastereomeric, polymorphic or stereoisomeric form, or any mixture thereof.

13. A compound according to claim 6, comprising an enantiomeric excess of the form which has an (S)-configuration at the center indicated by * in formula XVI.

14. A pharmaceutical composition comprising a pharmaceutically-acceptable excipient or diluent; and any compound according to claim 6, or an N-oxide, or a pharmaceutically-acceptable salt of any compound according to claim 6.

15. A method of treating a condition in a human or other mammal in which SP or NKA is implicated and antagonism of its action is desired, said method comprising:

administering a physiologically-effective amount of any compound according to claim 6; or administering a physiologically-effective amount of an N-oxide, or a pharmaceutically-acceptable salt of any compound according to claim 6.

16. The method of claim 15, wherein the condition is asthma in a human or other mammal suffering therefrom.

* * * * *